United States Patent [19]

Rumanowski

[11] Patent Number: 4,785,120

[45] Date of Patent: Nov. 15, 1988

[54] PROCESS FOR PREPARING SUBSTITUTED PHTHALIC ANHYDRIDES

[75] Inventor: Edmund J. Rumanowski, Dover, N.J.

[73] Assignee: Stauffer Chemical Company, Westport, Conn.

[21] Appl. No.: 78,124

[22] Filed: Jul. 27, 1987

[51] Int. Cl.$^4$ .............................................. C07D 307/89
[52] U.S. Cl. ..................................... 549/240; 549/243; 549/244; 549/245; 549/247
[58] Field of Search ............... 549/240, 243, 244, 245, 549/246, 247

[56] References Cited

U.S. PATENT DOCUMENTS 4,559,405 12/1985 Telschow ............................ 549/240
4,560,773 12/1985 Telschow ............................ 549/240

OTHER PUBLICATIONS

Neuman et al., J. Am. Chem. Soc., vol. 63 (1941) pp. 1542–1544.

Primary Examiner—Richard L. Raymond
Attorney, Agent, or Firm—Edwin H. Baker

[57] ABSTRACT

Yield and assay (purity) improvements in the reaction of bromine and the Diels-Alder addition product of maleic anhydride and a conjugated diene in the presence of a nitrogenous acid acceptor are realized in the instant process. The heating time after completion of bromine addition is increased to more completely eliminate hydrogen bromide from the reaction medium and thereby drive the reaction to completion. Also, the type of catalyst selected for use is one which will yield a phthalimide by-product impurity having a boiling point which differs enough from the boiling point of the desired product to allow for distillative separation of the impurity and desired product.

3 Claims, No Drawings

PROCESS FOR PREPARING SUBSTITUTED PHTHALIC ANHYDRIDES

BACKGROUND OF THE PRESENT INVENTION

In U.S. Pat. Nos 4,559,405 and 4,560,773 to J. Telschow, a process for preparing substituted phthalic anhydrides is described. The process involves reacting the Diels-Alder addition product of a conjugated diene and maleic anhydride (e.g., 4-methyl-1,2,3,6-tetrahydrophthalic anhydride) with bromine in the presence of a catalytic amount of an acid acceptor such as dimethylformamide or pyridine. The use of dimethylformamide catalyst (which is termed "most preferred" in those patents) has, however, given rise to less than desired yields and a higher than desired impurity level (e.g., of 4,N-dimethyl phthalimide) resulting in less than desired assay values. It was found, moreover, that the boiling point of the impurity was essentially the same as that of the desired substituted phthalic anhydride thereby precluding its separation or removal by distillation techniques. Hence, a need has arisen for an improved process of the general type illustrated in the Telschow patents which would result in a higher yield of product and a lower level of impurity.

SUMMARY OF THE PRESENT INVENTION

The present process is an improved version of the general type of reaction shown in the Telschow patents. It comprises two improvements. The first involves a more prolonged heating of the reaction mixture of Diels-Alder addition product, bromine and acid acceptor, after bromine addition, to increase the amount of by-product hydrogen bromide that is removed from the reaction mixture to thereby aid in driving the reaction to completion and thereby increase the yield of desired product. The assay (or purity) of the desire product was improved by using, in a preferred embodiment, as the acid acceptor, a higher molecular weight material than the dimethylformamide catalyst described as most preferred in the Telschow patents. This insured that any phthalimide impurity resulting from the reaction was of correspondingly higher molecular weight so as to have a boiling point of the desired substituted phthalic anhydride so as to be easily separable or removable from it by distillation procedures.

DETAILED DESCRIPTION OF THE PRESENT INVENTION

The general outlines of the present process are shown in U.S. Pat. Nos. 4,559,405 and 4,560,773, which are each incorporated herein by reference. The Diels-Alder addition product can be formed by reaction of maleic anhydride and a conjugated diene, such as isoprene, butadiene, 2,3-dimethylbutadiene, and the like. This reaction can take place at temperatures of from 55°–120° C. One such product is 4-methyl-1,2,3,6-tetrahydrophthalic anhydride (4-MPTA).

The addition product is advantageously added to the reaction vessel first and heated until it melts. The acid acceptor, of the type to be described later, is then added. Bromine is then added, while the reaction mixture is at elevated temperature, e.g., 100°–180° C., so that hydrogen bromide is evolved.

The process improvements of the present invention are twofold.

The first improvement, which is directed to increasing the yield of the desired substituted phthalic anhydride, involves the heating of the reaction mixture for an increased length of time to correspondingly increase the amount of hydrogen bromide evolved and thus aid in driving the reaction to completion. For example, in the case of the synthesis of 4-methyl phthalic anhydride, the Telschow patents shown heating for only about four hours at 150°–155° C. to complete liberation of hydrogen bromide. It has been found that a heating period of about 10–24 hours at even higher temperatures (e.g., about 180° C.) is even more advantageous.

The second improvement concerns the choice of catalyst. It was found that the Telschow procedure resulted in the formation of a phthalimide impurity whose structure, and hence molecular weight, was determined by the catalyst used. When 4-methyl phthalic anhydride was the desired product and dimethylformamide was the catalyst, a 4,N-dimethyl phthalimide resulted which happened to have a boiling point very close to the boiling point of the desired phthalic anhydride end product. This precluded its ready separation by distillation. Hence, the present invention also requires care in selecting the catalyst used so that the boiling point of any phthalimide impurity differs enough from the boiling point of the desired phthalic anhydride to allow for distillative separation or removal of the by-product. In the case of synthesis of 4-methyl phthalic anhydride, for example, it has been found that formamides of higher molecular weight than dimethylformamide (e.g., dibutylformamide) produced the desired results. Similarly, a secondary amine also containing a higher molecular weight alkyl group than methyl (e.g., di-n-butyl amine) was also satisfactory.

The present invention is further illustrated by the Examples which follow.

EXAMPLE 1

The following general procedure was utilized for the work reported herein. To 4-methyl-1,2,3,6-tetrahydrophthalic anhydride (4-MPTA) was added bromine in a 2% wt. excess over six hours at 135°–140° C. using 3% dimethylformamide catalyst. Then, after about one hour of extra heating at 155°–160° C. and one hour of sparging with nitrogen to eliminate hydrogen bromide, the 4-methylphthalic anhydride (4-MPA) product was distilled at total take-off at 10 mm Hg vacuum. Yields were generally in the range of 84–86% and the assay was 92–93% when the procedure was repeated.

A certain amount of undesired 4,N-dimethyl phthalimide impurity was detected. For example, the level of this impurity generally averaged about 1% if the 4-MPA was distilled in 10–24 hours at 10–15 mm vacuum at 160°–170° C. Distillation at 30–40 mm vacuum, 170°–180° C. pot temperature over 48–72 hours gave about 3% impurity.

A heat study of crude 4-MPA (84.2% assay) gave the following results:

| Time (hrs) | Temp (°C.) | Impurity (%)* |
| --- | --- | --- |
| 0 | 180 ± 3 | 0.04 |
| 2 | 180 ± 3 | 0.93 |
| 5 | 180 ± 3 | 1.64 |
| 25 | 240–260 | 5.38 |

*area % as determined by gas liquid chromatography in the crude product.

There is formation of the impurity that is directly related to the time that the crude product is exposed at the elevated temperatures. Since the impurity and the product have essentially the same boiling point, removal of the impurity is not possible.

EXAMPLE 2

This Example, using the general procedure of Example 1 with some changes, shows the results obtained when changes in catalyst were made:

| Run | Catalyst mole %* | % Yield 4-MPA | HPLC % Assay 4-MPA | % Impurity** |
|---|---|---|---|---|
| A (Control) | DMF-6.8 | 85.8 | 91.7 | 0.04 |
| B | DBA-6.8 | 86.7 | 91.0 | None |
| C | DBA-3.9 | 86.6 | 91.1 | None |
| D | DBF-6.0 | 84.0 | 92.7 | None |
| E*** | DBF-6.4 | 80.5 | 94.5 | None |

*mole % based on 4-MPTA: DMF = dimethylformamide; DBA = di-n-butyl amine, and DBF = di-n-butylformamide.
**impurity = 4,N—dimethyl phthalimide.
*** = used extended heating of crude 4-MPA at 180° C. ± 2° C. for twenty-four hours.

The extended heating at 180° C.±2° C. improved the assay of the distilled 4-MPA in Run E although the yield underwent a loss due to mechanical problems. The other runs had no elevated heating period.

EXAMPLE 3

This Example confirms the results obtained when the extra heating period used in Run E of Example 2 was employed:

| Run | Catalyst mole % | Extra Heat | Yield 4-MPA(%) | HPLC Assay 4-MPA(%) | % Impurity |
|---|---|---|---|---|---|
| A (Control) | DMF-6.8 | No | 85.8 | 91.7 | 0.04 |
| B | DBF-3.4 | 24 hrs | 89.4 | 96.8 | 0.1–0.2 |

There was a yield increase of 3.6% and a 5.1% assay elevation when the 180° C.±2° C. heating period was used in Run B. This was with a 50% reduction in catalyst amount versus Run A.

EXAMPLE 4

A series of additional catalyst screening runs were undertaken:

| Run | Catalyst mole % | Yield % MPA | HPLC Assay % | % Impurity |
|---|---|---|---|---|
| A (Control) | None | 92.5 | 91.7 | — |
| B | DBF-3.4 | 85.8* | 98.3* | <0.1 |
| C | DBF-3.4 | 89.4 | 95.1 | 0.1–0.2 |

*does not include low boiling fraction of additional 4.9% yield and 93.7% assay of 4-MPA.

The taking of a low boiling fraction (5%) in Run B raised the 4-MPA assay about 3% as compared to duplicate Run C.

EXAMPLE 5

This Example gives the results of various studies of the process using 1 mole of 4-MPTA and 2.02 moles bromine:

| Run | Catalyst mole % | 4-MPA Yield % | HPLC Assay % | Residue (gm) | Add. Heat. at 180° C. (hrs) |
|---|---|---|---|---|---|
| A (Control) | None | 92.5 | 91.7 | 13.5 | 24.5 |
| B | DMF-3 | 85.8 | 91.7 | 36 | 0 |
| C | DBF-3.2 | 89.4 | 97.8 | 24 | 24 |
| D | DBF-3.2 | 85.8* | 98.3* | 23 | 20 |
| E | DBF-3.0 | 85.4** | 98.1** | 27 | 17 |
| F | DBF-3.0 | 90.7 | 97.9 | 22 | 20 |
| G | DBF-1.5 | 95.1 | 96.2 | 13 | 10 |
| H | DBF-1.5 | 93.4 | 96.9 | 15.3 | 20 |

*not included low boiling fraction of additional 4.9% yield and 93.7% assay 4-MPA.
**not included low boiling fraction of additional 4.6% yield and 96.3% assay 4-MPA.

The 4-MPA yields increased about 5–10% and the assays increased about 5–6% by having an extended heating period of about 180° C.±2° C. versus Run B which had none. The DBF catalyst was just as effective at 50% of the standard rate of 3% for DMF. Also noteworthy is the lessened amount of residue remaining after distillation.

The foregoing Examples have only been presented to illustrate certain specific embodiments of the instant invention and should not, therefore, be construed in a limiting sense. The scope of protection which is sought is set forth in the Claims which follow.

I claim:

1. An improved process for forming methyl phthalic anhydride by reacting the Diels-Adler addition product of a conjugated diene and maleic anhydride with bromine in the presence of a catalytic amount of nitrogeneous acid acceptor, wherein the improvement comprises:
   (a) heating the admixture of addition product, acid acceptor and bromine for an increased length of time after bromine addition to increase the removal of by-product hydrogen bromide therefrom; and
   (b) utilizing as the nitrogenous acid acceptor a formamide of higher molecular weight than dimethylformamide or a secondary amine containing a higher molecular weight alkyl group than methyl.

2. The process as claimed in claim 1 wherein the formamide is di-n-butylformamide, the secondary amine is di-n-butylamine and the methyl phthalic anhydride is 4-methyl phthalic anhydride.

3. The process as claimed in claim 1 wherein the nitrogenous acid acceptor is di-n-butylformamide and the methyl phthalic anhydride is 4-methylphthalic anhydride.

* * * * *